United States Patent [19]

Padden et al.

[11] Patent Number: 5,569,172
[45] Date of Patent: *Oct. 29, 1996

[54] DEVICE FOR SUPPORTING AND IMMOBILIZING A PATIENT'S ARM AND SHOULDER AND METHOD THEREOF

[76] Inventors: John Padden, 214 E. Ruth Ave., #303, Phoenix, Ariz. 85020; Michael A. Steingard, 8602 N Starling La., Phoenix, Ariz. 85028

[*] Notice: The term of this patent shall not extend beyond the expiration date of Pat. No. 5,464,383.

[21] Appl. No.: 552,754

[22] Filed: Nov. 3, 1995

Related U.S. Application Data

[63] Continuation-in-part of Ser. No. 284,843, Aug. 2, 1994, Pat. No. 5,464,383.

[51] Int. Cl.[6] ............................................. A61F 5/00
[52] U.S. Cl. ............................. 602/20; 602/4; 128/878
[58] Field of Search ................................... 602/4–6, 20, 21, 602/60, 61, 62, 13; 128/878, 881, 882, 889, 892, DIG. 19, DIG. 20

[56] References Cited

U.S. PATENT DOCUMENTS

| | | | |
|---|---|---|---|
| 2,594,809 | 4/1952 | Sanders | 602/4 |
| 3,815,588 | 6/1974 | Klausner | 602/4 X |
| 4,285,337 | 8/1981 | Cosentino | 602/4 X |
| 4,372,301 | 2/1983 | Hubbard et al. | 602/4 X |
| 4,375,809 | 3/1983 | Meals | 128/878 |
| 4,510,928 | 4/1985 | Ackley | 602/4 |
| 4,598,701 | 7/1986 | Schaefer | 602/4 |
| 4,617,923 | 10/1986 | Coleman | 602/4 |
| 4,622,961 | 11/1986 | Christensen | 602/4 |
| 4,716,895 | 1/1988 | Marques et al. | 602/4 |
| 4,733,658 | 3/1988 | Ruthven, Jr. | 602/4 |
| 4,759,353 | 7/1988 | Melendez et al. | 602/4 |
| 4,836,195 | 6/1989 | Berrehail | 602/4 |
| 4,896,660 | 1/1990 | Scott | 602/4 |
| 4,971,041 | 11/1990 | Millikan et al. | 602/4 |
| 5,236,411 | 8/1993 | Backman | 602/13 |
| 5,291,903 | 3/1994 | Reeves | 128/878 |
| 5,334,132 | 8/1994 | Burkhead | 602/4 |
| 5,358,470 | 10/1994 | Johnson | 602/20 |
| 5,464,383 | 8/1995 | Padden | 602/20 |

*Primary Examiner*—Richard J. Apley
*Assistant Examiner*—Kim M. Lee
*Attorney, Agent, or Firm*—Harry M. Weiss; Jeffrey D. Moy; Harry M. Weiss & Associates, P.C.

[57] ABSTRACT

An orthopedic pillow device for supporting and immobilizing a patient's arm relative to a patient's shoulder is disclosed comprising a portable, L-shaped, reversible, pillow and a plurality of straps for attaching and securing the pillow to both the patient's upper torso and arm. The pillow is selectively attached to one of the patient's right arm and left arm and the patient's upper torso, for providing support and cushioning for both a lower and upper portion of the arm selected for support and for providing abduction of the arm selected for support with respect to the upper torso for reducing shoulder joint stress. The securing means is comprised of a removable shoulder strap, waist strap, forearm band, and upper arm strap.

16 Claims, 3 Drawing Sheets

DEVICE FOR SUPPORTING AND IMMOBILIZING A PATIENT'S ARM AND SHOULDER AND METHOD THEREOF

RELATED APPLICATION

This a continuation in part of U.S. Ser. No. 08/284,843, filed Aug. 2, 1994 now U.S. Pat. No. 5,464,383 in the name of the same applicants of this application.

BACKGROUND OF THE INVENTION

1. Field of the Invention

This invention relates generally to orthopedic devices and methods therefor, and more specifically relates to improved orthopedic pillow support devices used to hold, support, cushion and immobilize a patient's injured arm or a patient's arm with respect to a patient's injured shoulder and methods therefor.

2. Description of the Related Art

In the past, various types of orthopedic devices were created to support an arm and/or shoulder during post-surgical or non-surgical recovery from injury. These devices are often used prior to surgery as well. For example, to aid in the healing of and to provide relief to a shoulder suffering from any number of ailments such as rotator cuff injury, sprains, dislocations, humeral fractures and other injuries, it is critical to stabilize and immobilize the respective forearm and upper arm at a desired position with respect to the injured shoulder to prevent shoulder joint movement. It is further necessary to position the arm away from the upper torso at an abduction angle that is most conducive to reducing shoulder joint stress. It is also important to provide such support during both waking and sleeping hours while providing the utmost comfort and convenience to the patient.

The prior art includes a number of orthopedic devices for supporting an arm and shoulder. For example, one familiar device is the arm sling. It is simply comprised of material in which an arm, typically bent at the elbow at approximately a ninety degree angle, is placed in a shoulder strap for holding the material and arm in place. This type of device provides minimal arm and shoulder support but provides no immobilization of the arm and shoulder joints. It also generally does not provide cushioning for comfort.

U.S. Pat. No. 4,373,517 describes a device that supports an arm and immobilizes a shoulder. It is essentially a metal brace comprised of multiple rigid assemblies mounted to a patient's torso to support a rigid horizontal member, which, in turn, supports an arm in a horizontal-only position. This device suffers from numerous drawbacks. It is a complex device comprised of many rigid, metal parts and is consequently bulky, heavy, uncomfortable and not conducive for wearing over long periods of time. Furthermore, it limits the position of the arm to substantially the horizontal plane making it inflexible and unable to be worn in the recumbent (lying down) position. Therefore, a patient who needed the benefits of this device around the clock had to either remove the device to sleep in the recumbent position or sleep in an uncomfortable upright position.

Another orthopedic device developed was a shoulder immobilizer which provided a sling-type apparatus to hold an arm and a separate pillow device wrapped around a patient's waist upon which the arm rests. Weaknesses of this two-piece device are that it is only utilized for post-surgery situations and is not designed for recumbent use.

Moreover, none of the prior devices provided much versatility in terms of their application to a variety of injuries and conditions, flexibility of positioning the arm with respect to the patient's body, ease of use, and comfort, all in one device.

Accordingly, there existed a definite need to provide a new orthopedic support device that would be useful for a shoulder injury, arm injury or both; portable and lightweight; extremely comfortable to wear; easy to attach to the body; reversible for attachment to either the left arm and shoulder or right arm and shoulder; adjustable to the size of the patient and the desired position; and easier and less costly to manufacture than related devices. This device would be versatile enough for use in a wide variety of orthopedic applications ranging from non-surgical type arm or shoulder sprains, dislocations and fractures to post-surgical recovery periods such as that after a rotator cuff surgery or other shoulder surgeries. Furthermore, since patients who must wear the devices of the prior art to sleep must remain in the upright, sitting position, it was especially important to provide a device that could be worn in the recumbent, as well as upright positions.

U.S. Pat. No. 5,464,383, of which this is a continuation in part, addresses almost all of these needs—the device disclosed therein is useful for a shoulder injury, arm injury or both; portable and lightweight; extremely comfortable to wear; easy to attach to the body; reversible for attachment to either the left arm and shoulder or right arm and shoulder; adjustable to the size of the patient and the desired position; and easier and less costly to manufacture than related devices. However, the device in U.S. Pat. No. 5,464,383, while adequate for most applications, does not provide sufficient support for the patient's forearm, wrist and hand, with the result that the patient's hand and wrist can droop. Such drooping can, in certain specific instances, be uncomfortable for a patient, and a device that permits such drooping may in such instances be less therapeutic than a device that prevents wrist and hand drooping. Therefore, a need existed for a new orthopedic support device to address the issues listed above and, additionally, that would provide additional support to the forearm, wrist and hand of the patient, so as to minimize or prevent the drooping of the patient's wrist and/or hand and, generally, to further immobilize the patient's arm, including the patient's forearm, wrist, and hand.

SUMMARY OF THE INVENTION

In accordance with one embodiment of this invention, it is an object of this invention to provide an improved, reversible, orthopedic arm and shoulder support device that immobilizes both the shoulder and arm joints and provides abduction of the arm for reducing shoulder joint stress.

It is another object of this invention to provide an improved, reversible, orthopedic arm and shoulder support device that immobilizes the wrist and hand for reducing stress and/or harm caused by the drooping of the hand while the support device is worn.

It is still another object of this invention to provide a new orthopedic pillow support device that is light, low cost, easy to attach to the body and comfortable to wear.

It is a further object of this invention to provide an orthopedic arm and shoulder pillow device for use while the patient is in the recumbent, as well as upright, positions.

It is yet another object of this invention to provide a method for a new and improved, reversible, orthopedic arm and shoulder support device that immobilizes both the shoulder and arm joints.

BRIEF DESCRIPTION OF THE PREFERRED EMBODIMENTS

In accordance with one embodiment of this invention, an orthopedic pillow device for supporting and immobilizing a patient's arm relative to a patient's shoulder is disclosed comprising, in combination, a portable, reversible, pillow support means for selective attachment to one of the patient's right arm and left arm and the patient's upper torso, wherein the support means comprises an L-shape pillow means for providing support and cushioning for both a lower and upper portion of the arm selected for support, and for providing abduction of the lower and upper portions of the arm selected for support with respect to the upper torso for reducing joint stress in the shoulder, and a securing means coupled to the support means for securing the support means to both the patient's arm and upper torso.

The support means comprises an inner material having a long member coupled at one end thereof to one end of a short member forming an L-shape, and an outer casing conforming to the L-shape of the inner material for containing the inner material. The inner material comprises a fiberfill material stuffed in a casing. The outer casing comprises sealable opening means for providing access to the inner material for removing the inner material from the outer casing.

The securing means comprises a first securing means for securing the support means to the patient's upper torso and a second securing means for securing the support means to the patient's arm. The first strap means comprises a waist strap coupled to the long member of the support means for securing to a portion of the patient's waist and a shoulder strap coupled at one end thereof to the unconnected end of the long member and coupled at the other end thereof to the unconnected end of the short member for securing the support means to the patient's shoulder. The shoulder strap is removable. The second securing means comprises an upper arm strap coupled to the short member for securing the upper arm to the support means and a forearm band coupled to the long member for securing a portion of the patient's forearm, the patient's wrist, and a portion of the patient's hand to the support means.

In accordance with another embodiment of this invention, an orthopedic pillow support device is disclosed wherein the inner material is comprised of a pre-formed foam material.

In accordance with yet another embodiment of this invention, an orthopedic pillow device is disclosed wherein the inner material is comprised of an inflatable air bladder.

In accordance with still another embodiment of this invention, a method of providing an orthopedic arm and shoulder support device is disclosed, comprising the steps of providing a portable, reversible, pillow support means for selective attachment to one of the patient's right arm and left arm and the patient's upper torso, the support means comprising an L-shape pillow means for providing support and cushioning for both a lower and upper portion of the arm selected for support, and a securing means coupled to the support means for securing the support means to both the patient's arm and upper torso.

The foregoing and other objects, features, and advantages of the invention will be apparent from the following, more particular, description of the preferred embodiments of the invention, as illustrated in the accompanying drawings.

DESCRIPTION OF THE PREFERRED EMBODIMENTS

Figure 1:
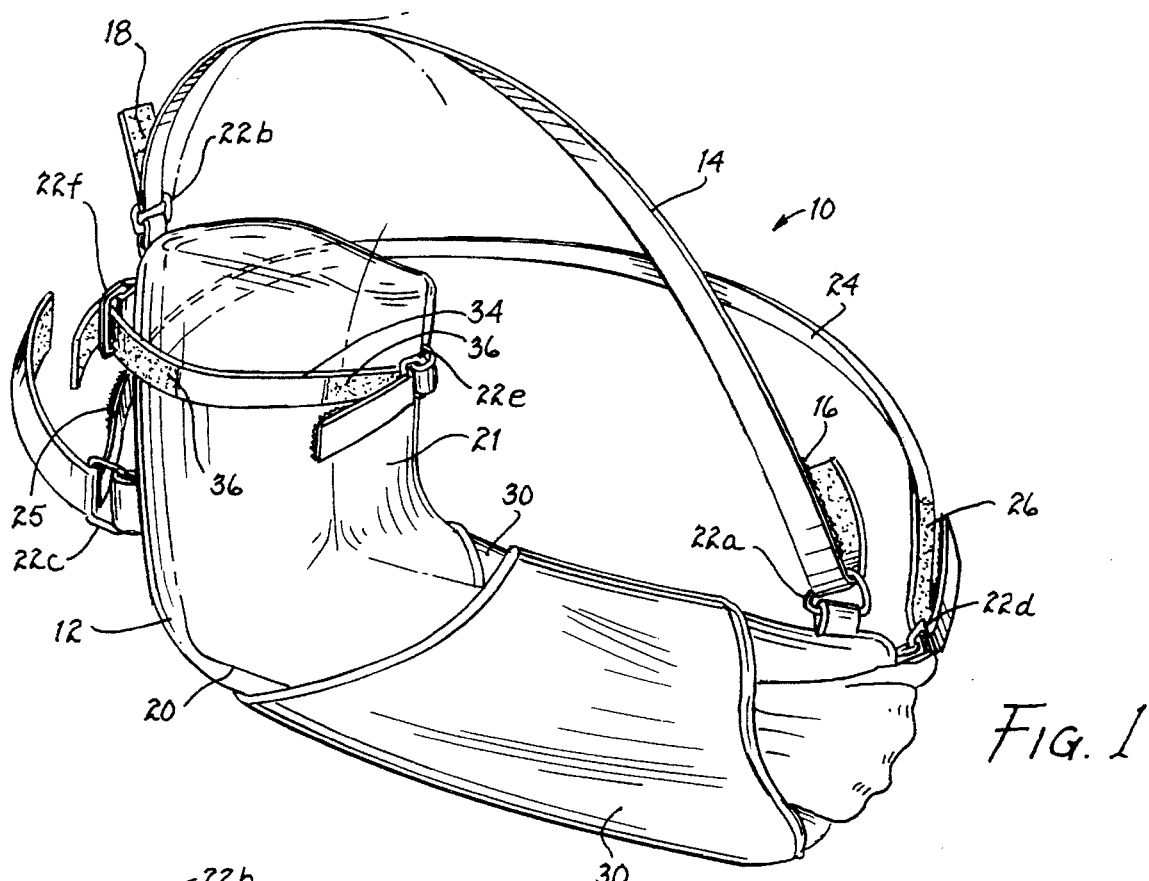
FIG. 1 is a perspective view of the preferred embodiment of the arm and shoulder support device, as shown with an arm inserted therein.
Figure 2:
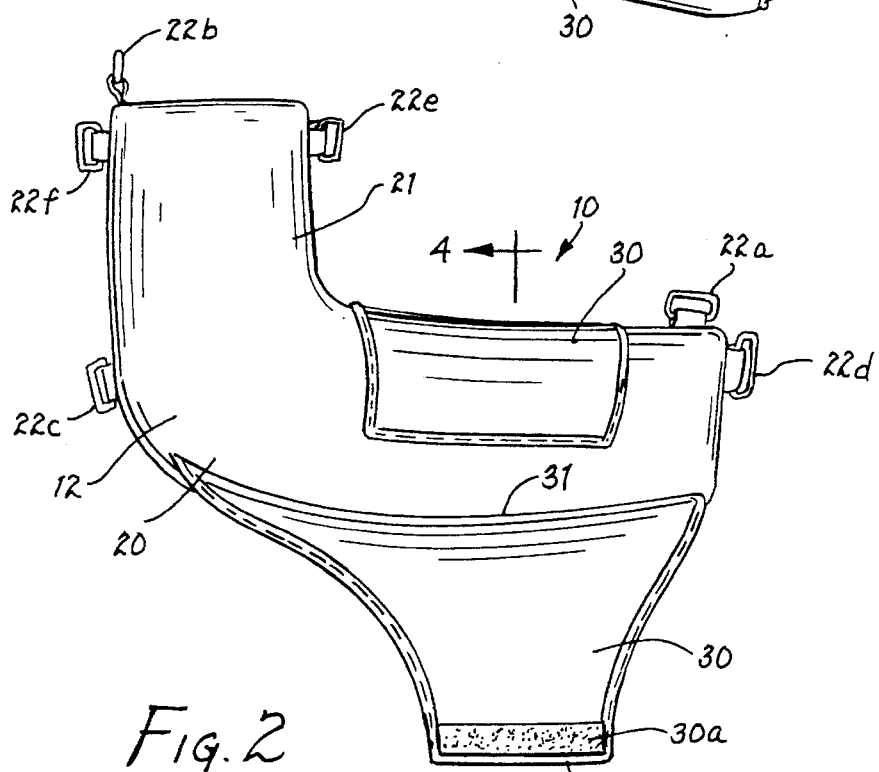
FIG. 2 is a perspective view of the preferred embodiment of the arm and shoulder support device of FIG. 1, as shown without an arm inserted therein.

Referring to FIGS. 1 and 2, a portable, reversible, arm and shoulder, pillow, support device 10, or simply, support device 10 is provided. The support device 10 is comprised of a pillow support 12, which is further comprised of a long member 20 coupled to a short member 21 forming an L-shape, and D-rings 22a, 22b, 22c, 22d, 22e, and 22f, coupled to pillow support 12 providing attachments for various straps to the pillow support 12. The pillow support 12 additionally comprises a securing portion which is further comprised of a first securing portion, consisting of straps 14, 24, for attaching the pillow support 12 to a patient's upper torso and a second securing portion, consisting of forearm bands 30 and strap 34, for attaching the pillow support 12 to one of the patient's right arm and left arm, including a portion of the patient's forearm, the patient's wrist, and a portion of the patient's hand.

Figure 8:
FIG. 8 is a perspective view of the support device of FIG. 1 as worn by a person in the recumbent position.

The first securing portion is specifically comprised of a shoulder strap 14 and a waist strap 24. The shoulder strap 14 is looped at one end thereof through a D-ring 22a. This end of shoulder strap 14 further carries a hook and loop assembly 16, common known under the tradename VELCRO, for securing shoulder strap 14 to D-ring 22a. The hook and loop assembly 16 further provides a means for adjusting the length of shoulder strap 14 to the patient's preference. Similarly, the opposite end of shoulder strap 14 carries a hook and loop assembly 18 for securing it to D-ring 22b and for providing a second means for adjusting the length of shoulder strap 14. Both ends of shoulder strap 14 are provided with hook and loop assemblies 16 and 18 as the means for securing it to the pillow means 12 in order to provide the option of completely removing the shoulder strap 14 from the support device 10. An embodiment with the shoulder strap 14 removed is shown in FIG. 8 and described below.

Waist strap 24 is looped at one end through D-ring 22c that is located substantially at a back portion of pillow support 12 near the intersection of long member 20 and short member 21, and is provided with hook and loop assembly 25 for adjustably securing the support device 10 to the patient's upper torso. The opposite end of waist strap 24 is looped through D-ring 22d that is located substantially at the open end of long member 20 and is provided with hook and loop assembly 26 for adjustably securing the support device 10 to the patient's upper torso.

The second securing portion is specifically comprised of forearm bands 30 and an upper arm strap 34. The bottom portions 31 of forearm bands 30 are each fixedly connected to the pillow support 12 along a line that is substantially at the confluence of the long member 20 and the bottom portion 61 of the pillow support 12, and the length of the bottom portions 31 is substantially equal to the length of long member 20 (see FIG. 3). Forearm bands 30 are each comprised of hook and loop assemblies 30a (see FIG. 2), whereby hook strip portions are located on the top portions 33 of forearm bands 30, which hook strips may each be mated with the long member 20 or with the surface area of the forearm band 30 not in use, the material of which long member 20 and forearm bands 30 serves as a loop strip portion. For example, as shown in FIG. 2, one of the forearm bands 30 is wrapped around long member 20 and is secured to long member 20 with the hook and loop assembly 30a (not shown). The length of the top portions 33 of bands 30 is slightly less than the distance between the intersection of the long member 20 and the short member 21 and D-ring 22a, so that the top portions 33 of forearm bands 30 may pass over the top of long member 20 and be secured to the opposite side of the long member 20 without any portion of forearm bands 30 coming into contact with the short member 21 or D-ring 22a. The side portions of forearm bands 30 are angled so as to permit the securing of the top portions 33 of the forearm bands 30 to the opposite side of long member 20, without any portion of forearm bands 30 coming into contact with the short member 21 or the D-ring 22a.

Referring now to FIG. 1, a first forearm band 30 is wrapped around long member 20 and a portion of the patient's forearm, the patient's wrist, and a portion of the patient's hand and is secured to a second forearm band 30 with the hook and loop assembly 30a. This is a significant improvement over the attachment in our prior application as set forth above, in order to prevent undesired drooping of the wrist and/or hand. In the event that the second forearm band 30 is not first secured to long member 20 prior to the insertion of a portion of the patient's forearm, the patient's wrist, and a portion of the patient's hand, the forearm band 30 may be secured directly to the long member 20 with the hook and loop assembly 30a (not shown). Upper arm strap 34 is looped at one end through D-ring 22e that is located at an inner portion of short member 21, and is looped at the second end through D-ring 22f that is located at an outer portion of short member 21. The uncoupled ends of the upper arm strap 34 carry hook and loop assemblies 36 for securing the upper arm to the pillow support 12.

It should be understood that support device 10 is reversible and may be used to support and stabilize either a patient's right arm, shoulder, wrist, and hand or a patient's left arm, shoulder, wrist, and hand.

Figure 3:
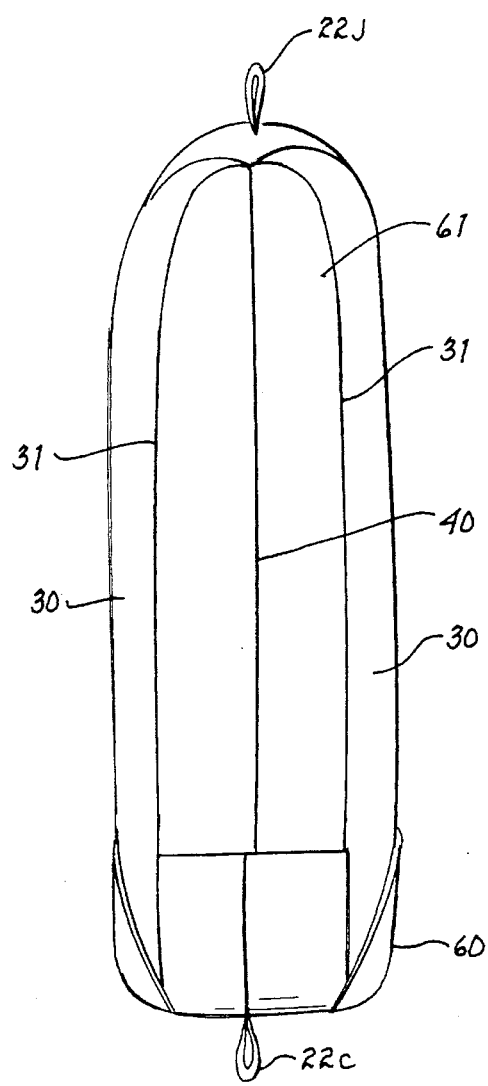
FIG. 3 is a bottom view of the of the support device of FIG. 1 taken along the line 3—3.

Referring to FIG. 3, the bottom portion 61 of the pillow support 12 is shown. An outer casing 60 surrounds the long member 20, the short member 21, and the bottom portion 61 of pillow support 12. The bottom portion 61 comprises a hook and loop assembly 40, which assembly allows for access to and removal of the inner material (not shown in FIG. 3) of pillow support 12 from the outer casing 60 so that the outer casing 60 may be cleaned. After cleaning and drying the outer casing 60, the inner material may be easily reinserted and the outer casing 60 may be closed.

Figure 4:
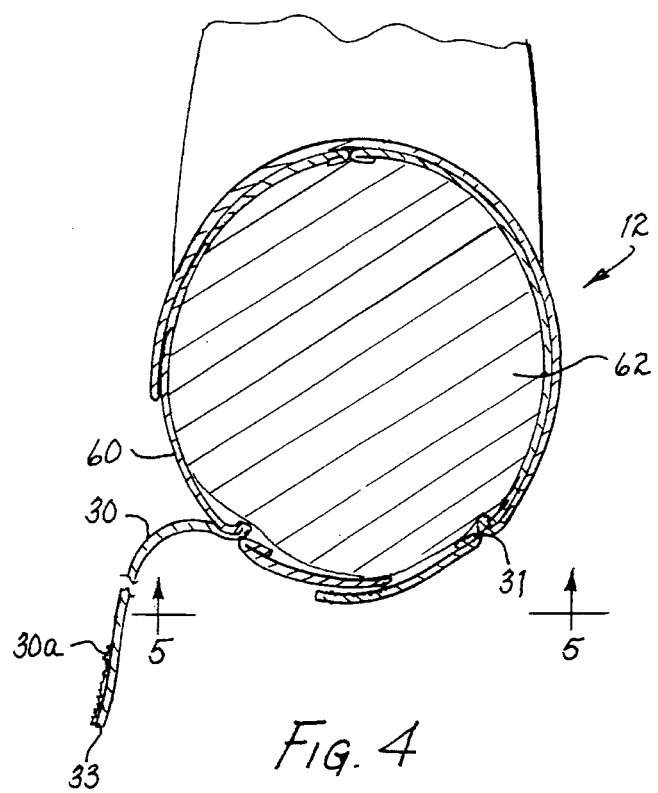
FIG. 4 is a cross-sectional view of the long member of the support device of FIG. 1 taken along the line 4—4 showing a fiberfill inner material or a pre-formed material.

Referring to FIG. 4, a cross-sectional view of a portion of pillow support 12, taken along line 4—4 of FIG. 2, is provided. The outer casing 60 contains an inner material 62, which may be comprised of a fiberfill material or a preformed foam material. Pillow support 12 may be manufactured in a variety of thicknesses resulting in a plurality of support devices 10, each providing a different abduction angle between the patient's arm and upper torso. Offering more than one support device 10 having different abduction angles provides the attending physician or patient the option of selecting the support device 10 best suited to the patient's conditions and needs.

Figure 5:
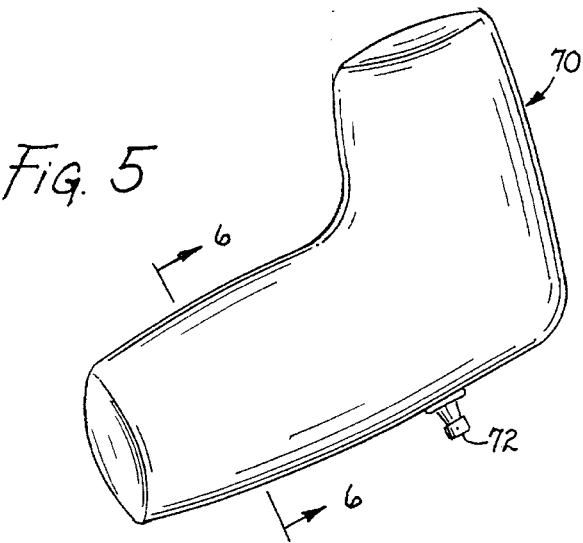
FIG. 5 is a perspective view of the pillow support member of FIG. 1 in another embodiment providing an inflatable air bladder for the inner material.

Referring to FIG. 5, an alternative embodiment of the inner material of pillow support 12 is shown. It is comprised of an inflatable air balloon 70 and nozzle 72 for inflating and deflating the air balloon 70. The advantage of this embodiment is that pillow support 12 may be inflated to varying degrees determined by the patient's preference or physician's prescription. As the degree of inflation increases, the inflatable air balloon 70 becomes harder or stiffer and the abduction angle formed between the arm and upper torso also increases. In essence, this embodiment allows a single support device 10 to be customized to the patient's needs.

Figure 6:
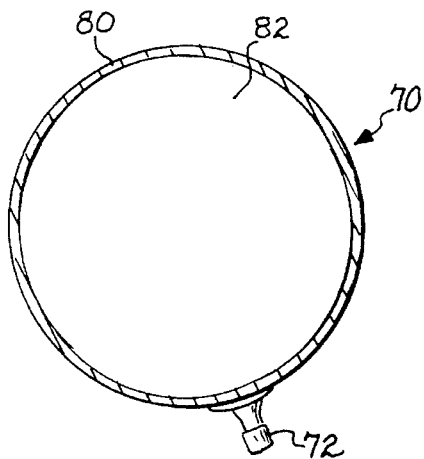
FIG. 6 is a cross-sectional view of the long member of the support device of FIG. 5 taken along the line 6—6.

Referring to FIG. 6, a cross-sectional view of the long member of the inflatable air balloon 70 of FIG. 5 (taken along line 6—6) is provided. It is comprised of an outer rubber-type material 80 and is filled with a gas 82, such as air, through nozzle 72.

Figure 7:
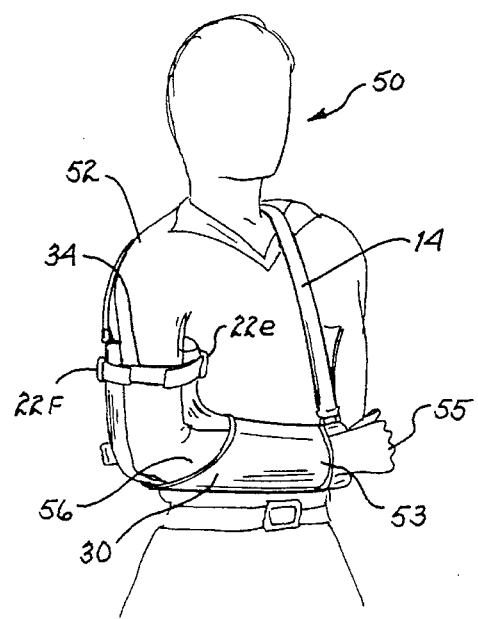
FIG. 7 is a perspective view of the support device of FIG. 1 as worn by a person in the upright position.

Referring to FIG. 7, patient 50 is wearing the support device 10 of FIG. 1 to support and stabilize his right shoulder 52, right arm 54, right wrist 53, and a portion of right hand 55 while the patient 50 is in the upright position. Specifically, upper arm strap 34 is wrapped around the upper arm 58 to secure it to the short member 21. Forearm band 30 secures the patient's forearm 56, wrist 53, and a portion of hand 55 to the desired location along long member 20. Waist strap 24 (not shown in FIG. 7) is wrapped around the waist and back of patient 50 and tightened and secured through the hook and loop assemblies 25 and 26 and D-rings 22c and 22d (see FIG. 1). (It is understood that if the pillow support 12 is to be used for the left arm, second forearm band 30 secures the patient's forearm, wrist, and a portion of patient's hand to the desired location along long member 20). Waist strap 24 (see FIG. 1) secures and immobilizes the patient's arm 54 to the patient's upper torso. Shoulder strap 14 positions and holds forearm 56 at a desired angle relative to the upper arm 58. Taken together, the securing portions 14, 24, 30, 31, and 34 serve to hold, secure and comfortably immobilize the right arm 54 of patient 50, thereby comfortably immobilizing his right shoulder 52 as well.

Referring to FIG. 8, patient 88 is shown wearing the support device 10 on the left arm in the recumbent position. In this embodiment, the shoulder strap 14 is typically removed.

While the invention has been particularly shown and described with reference to the preferred embodiments thereof, it will be understood by those skilled in the art that the foregoing and other changes in form and details may be made therein without departing from the spirit and scope of the invention.

What is claimed is:

1. An orthopedic pillow device for supporting and immobilizing a patient's arm relative to a patient's shoulder, comprising, in combination:

portable, reversible, pillow support means for selective attachment to one of the patient's right arm and left arm and the patient's upper torso, said support means comprising L-shape pillow means, having a substantially elliptical cross-sectional shaped pillow configuration, for being configured to extend in an L-shaped configuration from just below a person's armpit to about the end of a person's hand for providing support and cushioning for both a lower and upper portion of the arm selected for support including a portion of the forearm, the wrist and a portion of the hand of said arm, and for providing abduction of said lower and upper portions of the arm selected for support with respect to said upper torso for reducing joint stress of said shoulder, said support means having a thickness along its L-shaped configuration and an outer surface portion means for supporting an inner portion of said selected arm extending substantially in one plane downward and in said L-shaped configuration from the armpit of said selected arm to said upper and said lower portions of said selected arm and an inner surface portion means for extending inwardly from the armpit of said selected arm and in said L-shaped configuration parallel to and adjacent to a front portion of a person's torso;

securing means coupled to said support means comprising first securing means for securing said support means to said patient's upper portion of the selected arm and second securing means adapted to extend along and about a substantial portion of the lower portion of the selected arm including the wrist for securing said support means to said patient's lower portion of the selected arm including a portion of said forearm, said wrist and said portion of said hand of said arm.

2. The device of claim 1 wherein said support means comprises an inner material having a long member coupled at one end thereof to one end of a short member forming said L-shaped configuration, and an outer casing conforming to said L-shaped configuration of said inner material for containing said inner material.

3. The device of claim 2 wherein said inner material is a material selected from a group consisting of a pre-formed foam material and a fiberfill material stuffed in a casing.

4. The device of claim 2 wherein said inner material comprises an inflatable air bladder.

5. The device of claim 2 wherein said outer casing comprises hook and loop assembly means for providing access to said inner material for removing said inner material from said outer casing.

6. The device of claim 2 wherein said first securing means comprises a waist strap coupled to said long member of said support means for securing to a portion of said patient's waist and a shoulder strap coupled at one end thereof to an end of said long member not coupled to said short member and coupled at the other end thereof to an end of said short member not coupled to said long member for securing said support means to said patient's shoulder.

7. The device of claim 6 wherein said shoulder strap is removable.

8. The device of claim 2 wherein said second securing means comprises, in combination:

an upper arm strap coupled to said short member for securing an upper portion of said arm to said support means;

a band of material coupled to said long member for securing a portion of said patient's forearm, said patient's wrist, and a portion of said patient's hand to said support means; and wherein said band of material comprises a bottom portion that is substantially the length of said long member and a top portion having a length that is less than the distance between said short member and the open end of said long member.

9. A method for providing an orthopedic pillow device for supporting and immobilizing a patient's arm relative to a patient's shoulder comprising the steps of:

providing a portable, reversible, pillow support means for selective attachment to one of the patient's right arm and left arm and the patient's upper torso, said support means comprising L-shape pillow means, having a substantially elliptical cross-sectional shaped pillow configuration, for being configured to extend in an L-shaped configuration from just below a person's armpit to about the end of a person's hand for providing support and cushioning for both a lower and upper portion of the arm selected for support including a portion of the forearm, the wrist and a portion of said hand of said arm, and for providing abduction of said lower and upper portions of the arm selected for support with respect to said upper torso for reducing joint stress of said shoulder, said support means having a thickness along its L-shaped configuration and an outer surface portion means for supporting an inner portion of said selected arm extending substantially in one plane downward and in said L-shaped configuration from the armpit of said selected arm to said upper and said lower portions of said selected arm and an inner surface portion means for extending inwardly from the armpit of said selected arm and in said L-shaped configuration parallel to and adjacent to a front portion of a person's torso; and coupling securing means to said support means comprising first securing means for securing said support means to said patient's upper portion of the selected arm and second securing means adapted to extend along and about a substantial portion of the lower portion of the selected arm including the wrist for securing said support means to both said patient's lower portion of the selected arm including a portion of said forearm, said wrist and a portion of said hand of said arm.

10. The method of claim 9 wherein said support means comprises an inner material having a long member coupled at one end thereof to one end of a short member forming said L-shaped configuration, and an outer casing conforming to said L-shaped configuration of said inner material for containing said inner material.

11. The method of claim 9 wherein said inner material is a material selected from a group consisting of a pre-formed foam material and a fiberfill material stuffed in a casing.

12. The method of claim 9 wherein said inner material comprises an inflatable air bladder.

13. The method of claim 10 wherein said outer casing comprises hook and loop assembly means for providing access to said inner material for removing said inner material from said outer casing.

14. The method of claim 10 wherein said first securing means comprises a waist strap coupled to said long member of said support means for securing to a portion of said patient's waist and a shoulder strap coupled at one end thereof to an end of said long member not coupled to said short member and coupled at the other end thereof to an end of said short member not coupled to said long member for securing said support means to said patient's shoulder.

15. The method of claim 14 wherein said shoulder strap is removable.

16. The method of claim 10 wherein said second securing means comprises:

an upper arm strap coupled to said short member for securing an upper portion of said arm to said support means;

a band of material coupled to said long member for securing a portion of said patient's forearm, said patient's wrist, and a portion of said patient's hand to said support means; and wherein said band of material comprises a bottom portion that is substantially the length of said long member and a top portion having a length that is less than the distance between said short member and the open end of said long member.

* * * * *